(12) United States Patent
Borsari

(10) Patent No.: US 11,565,065 B2
(45) Date of Patent: Jan. 31, 2023

(54) FACE MASK FOR NON-INVASIVE MECHANICAL VENTILATION WITH LOW VALUE OF $CO_2$ REBREATHING

(71) Applicant: DIMAR S.R.L., Medolla (IT)

(72) Inventor: Maurizio Borsari, Medolla (IT)

(73) Assignee: DIMAR S.R.L., Medolla (IT)

( * ) Notice: Subject to any disclaimer, the term of this patent is extended or adjusted under 35 U.S.C. 154(b) by 521 days.

(21) Appl. No.: 16/611,302

(22) PCT Filed: May 10, 2018

(86) PCT No.: PCT/IB2018/053254
§ 371 (c)(1),
(2) Date: Nov. 6, 2019

(87) PCT Pub. No.: WO2018/207127
PCT Pub. Date: Nov. 15, 2018

(65) Prior Publication Data
US 2020/0164168 A1 May 28, 2020

(30) Foreign Application Priority Data

May 11, 2017 (IT) .................. 102017000051148

(51) Int. Cl.
*A61M 16/06* (2006.01)
*A61M 16/08* (2006.01)
*A61F 9/04* (2006.01)

(52) U.S. Cl.
CPC .... *A61M 16/0616* (2014.02); *A61M 16/0683* (2013.01); *A61M 16/0816* (2013.01); *A61F 9/04* (2013.01); *A61M 2202/0225* (2013.01)

(58) Field of Classification Search
CPC ........ A61M 16/00; A61M 16/06–0694; A61M 16/0816; A61M 2202/0225; A61F 9/04;
(Continued)

(56) References Cited

U.S. PATENT DOCUMENTS

| 1,352,818 A | * | 9/1920 | Lamb | ..................... A62B 18/02 |
| | | | | 128/201.15 |
| 4,328,797 A | * | 5/1982 | Rollins, III | ........... A61M 16/06 |
| | | | | 128/912 |

(Continued)

FOREIGN PATENT DOCUMENTS

EP   0 511 593 A1   11/1992
EP   3 067 085 A1   9/2016
(Continued)

OTHER PUBLICATIONS

Third Party Observation issued May 17, 2021 in corresponding Patent Application No. 18731171.7, 5 pages.
(Continued)

*Primary Examiner* — Margaret M Luarca
*Assistant Examiner* — Cana A Gallegos
(74) *Attorney, Agent, or Firm* — Oblon, McClelland, Maier & Neustadt, L.L.P.

(57) ABSTRACT

A face mask (also called full face) for respiratory therapy, in particular for non-invasive mechanical ventilation, has a low value of $CO_2$ rebreathing. The mask includes a shaped shell to cover at least the mouth, the nose and the eyes of a patient when the mask is worn, and includes, on said shaped shell an inlet fitting for the connection to a pipe through which a ventilation apparatus supplies the mask with a mixture of air and oxygen, and an outlet fitting, separate from said inlet fitting, for the discharge of air exhaled by the patient. With this arrangement, the mask allows drastically reducing the phenomenon of carbon dioxide rebreathing, which is very harmful for the patient subjected to ventilation.

8 Claims, 4 Drawing Sheets

(58) Field of Classification Search
CPC .. A62B 18/02; A62B 7/00; A62B 9/00; A62B 9/06
See application file for complete search history.

(56) References Cited

U.S. PATENT DOCUMENTS

| | | | |
|---|---|---|---|
| 4,971,051 A | 11/1990 | Toffolon | |
| 2003/0111080 A1 | 6/2003 | Olsen et al. | |
| 2007/0113854 A1 | 5/2007 | Mcauliffe | |
| 2010/0116276 A1* | 5/2010 | Bayasi | A61M 16/06 128/207.12 |
| 2010/0258133 A1* | 10/2010 | Todd | A61M 16/0816 128/207.12 |
| 2011/0232647 A1* | 9/2011 | Ho | A61M 16/06 128/206.28 |
| 2013/0102916 A1 | 4/2013 | Colbaugh et al. | |
| 2014/0034057 A1 | 2/2014 | Todd et al. | |
| 2016/0263338 A1 | 9/2016 | Borsari | |
| 2016/0271351 A1* | 9/2016 | Frater | A61M 16/0057 |
| 2016/0271355 A1 | 9/2016 | Todd et al. | |

FOREIGN PATENT DOCUMENTS

| | | |
|---|---|---|
| WO | WO 2009/063402 A1 | 5/2009 |
| WO | WO 2011/077407 A3 | 6/2011 |
| WO | WO 2011/161561 A1 | 12/2011 |
| WO | WO 2018/116040 A1 | 6/2018 |

OTHER PUBLICATIONS

Luca Cabrini et al., "A novel non-invasive ventilation mask to prevent and manage respiratory failure during fiberoptic bronchoscopy and transesophageal echocardiography", Expert Opinion, vol. 7, 2015, pp. 297-303.
Alberto Zangrillo et al., "Prolonged transesophageal echocardiography during percutaneous closure of the left atrial appendage without general anesthesia: the utility of the Janus mask", Can J Anesth/J Can Anesth , Apr. 26, 2016, pp. 962-965.
Biomedical 2012, Company Profile, 2 pages.
International Search Report dated Aug. 13, 2018 in PCT/IB2018/053254 filed on May 10, 2018.

* cited by examiner

CPAP

PSV

FACE MASK FOR NON-INVASIVE MECHANICAL VENTILATION WITH LOW VALUE OF $CO_2$ REBREATHING

FIELD OF THE INVENTION

The present invention relates to a face mask (also called full face) for respiratory therapy, in particular for non-invasive mechanical ventilation, with a low value of $CO_2$ rebreathing.

Masks for the administration to a patient of a respiratory therapy at home or at the hospital are known, which can be divided into: nasal masks, covering only the nose, mouth-nasal masks, also called facial, covering the nose and mouth and full face masks, also called facial or full face or total, covering the entire face and therefore also the region of the eyes.

The mask object of the present invention is a full face mask for the non-invasive mechanical ventilation of a patient.

The masks of this type generally comprise a rigid plastic shell, three-dimensionally shaped to receive the patient's face, and provided along the entire perimeter to be placed on the patient's face with a sealing gasket of elastomeric material.

The rigid shell further comprises an inlet fitting for the mixture of air and oxygen coming from a ventilation apparatus and attachment points of means for fixing the mask to the head of the patient, consisting of a so-called neckband, which keeps the mask on the head of the patient in the most stable and adherent possible way.

The respiratory therapy masks known to date further comprise a neckband which can be attached to the mask at four points.

The Applicant has also developed a total mask for the non-invasive mechanical ventilation of a patient comprising a neckband attached to the mask at five attachment points.

Preferably, the mask according to the present invention is a mask with five attachment points, however the inventive concept underlying the invention described herein may also be applied to "full face" masks having different configurations of the neckband.

PRIOR ART

It is known that patients undergoing respiratory therapy due to conditions of hypoxia, cyanosis, dyspnoea, ortopnea, gasping, changes in respiration rate, alterations in the state of consciousness and/or subject to pathological respiratory noises, such as for example rales, wheezing, whiffs and/or whistles, require the administration of oxygen that can occur through the use of different devices.

Such devices may include, for example, nasal cannulas, simple face masks, Venturi masks, nasopharyngeal tubes, transtracheal catheters, endotracheal tubes or cannulas, NIMV (Non-Invasive Mechanical Ventilation) masks, CPAP (Continuous Positive Airway Pressure) and so on, according to what is known from the prior art.

When using such devices for assisted patient ventilation, it is very important to monitor the levels of carbon dioxide ($CO_2$) expelled by the patient by breathing.

This problem is even more pronounced in the case of use of total masks for non-invasive mechanical ventilation, since the prior art masks were found to have a double drawback.

The Applicant has identified these drawbacks as a result of experimental tests, conducted using total masks in different modes of assisted ventilation (for example CPAP—Continuous Positive Airway Pressure, PSV—Pressure Support Ventilation).

A first problem consists in the fact that inside the rigid shell made of plastic material that receives the patient's face, of considerable size, there is a consistent stagnation of $CO_2$. In fact, carbon dioxide tends to stagnate inside the full face mask, with very high concentrations of $CO_2$, which involves a certain volume of $CO_2$ which is re-breathed by the patient, drastically worsening the so-called "rebreathing" of $CO_2$.

A second problem that negatively affects the rebreathing of $CO_2$ by the patient relates to the ventilation tube.

In configurations of known types of masks, in which the ventilation tube is connected to the masks by means of a fitting, the section of ventilation pipe which connects to the mask further increases the volume of stagnation of CO2, since the carbon dioxide exhaled by the patient is at least partially reintroduced into the mask with the next step of intake of ventilation air flow.

In order to reduce this second drawback, it is known from the prior art to provide suitable so-called non-rebreathing valves, which however considerably increase the expiratory resistance for the patient, thus worsening the efficiency of the ventilation.

The persistence of problems that do not allow an adequate elimination or expulsion of carbon dioxide from the body can determine the consequent increase in the concentration of carbon dioxide in the blood. This phenomenon, called hypercapnia, can have serious consequences on patients by exerting a depressive effect on the central nervous system, with headaches, confusion and even coma, up to death by hypercapnia.

It is therefore essential to reduce as much as possible, if it is not possible to eliminate completely, the phenomenon of carbon dioxide rebreathing which has been found to be particularly burdensome in the case of use of full face masks.

Until now, the problem of rebreathing has been much underestimated, although known with the definition of "dead space", and the use of anti-rebreathing valves had led operators and industry experts to believe that they had limited the problem. However, as said, in full face masks the use of anti-rebreathing valves according to what is known from the prior art has no efficacy in reducing the problem of the stagnation of $CO_2$ which occurs in the inner volume of the mask itself.

This particular problem has never been quantified, nor put under investigation, in the sector due to the lack of adequate equipment, while the Applicant has investigated in depth the phenomenon of CO2 stagnation and rebreathing in a full face mask, determining to what extent masks of a known type expose the patient to the serious risks of increasing the concentration of carbon dioxide in the blood mentioned above.

SUMMARY OF THE INVENTION

The task of the present invention is to obviate the drawbacks affecting face masks for non-invasive assisted ventilation of the full-face type, with particular reference to the phenomenon of $CO_2$ rebreathing.

Within this task, the object of the present invention is to provide a face mask for assisted ventilation of the full-face type which allows reducing, if not completely eliminating, the stagnation of carbon dioxide exhaled by the patient inside the shell of the mask itself.

A further object of the present invention is to provide a face mask for assisted ventilation which allows eliminating, or at least reducing, the phenomenon of $CO_2$ rebreathing without using valves or similar devices that can increase the expiratory resistance or not completely fulfill the purpose.

This task, as well as the above objects and others that will become apparent hereinafter, are achieved by a face mask for non-invasive respiratory therapy of the full face type with a low value of $CO_2$ rebreathing as set forth in claim 1.

Further features are described in the dependent claims.

LIST OF FIGURES

The features and the advantages of the respiratory mask with a low value of carbon dioxide rebreathing according to the present invention will become apparent from the following detailed description, given by way of a non-limiting example, with reference to the accompanying schematic drawings, in which.

DETAILED DESCRIPTION OF THE INVENTION

Figure 1:
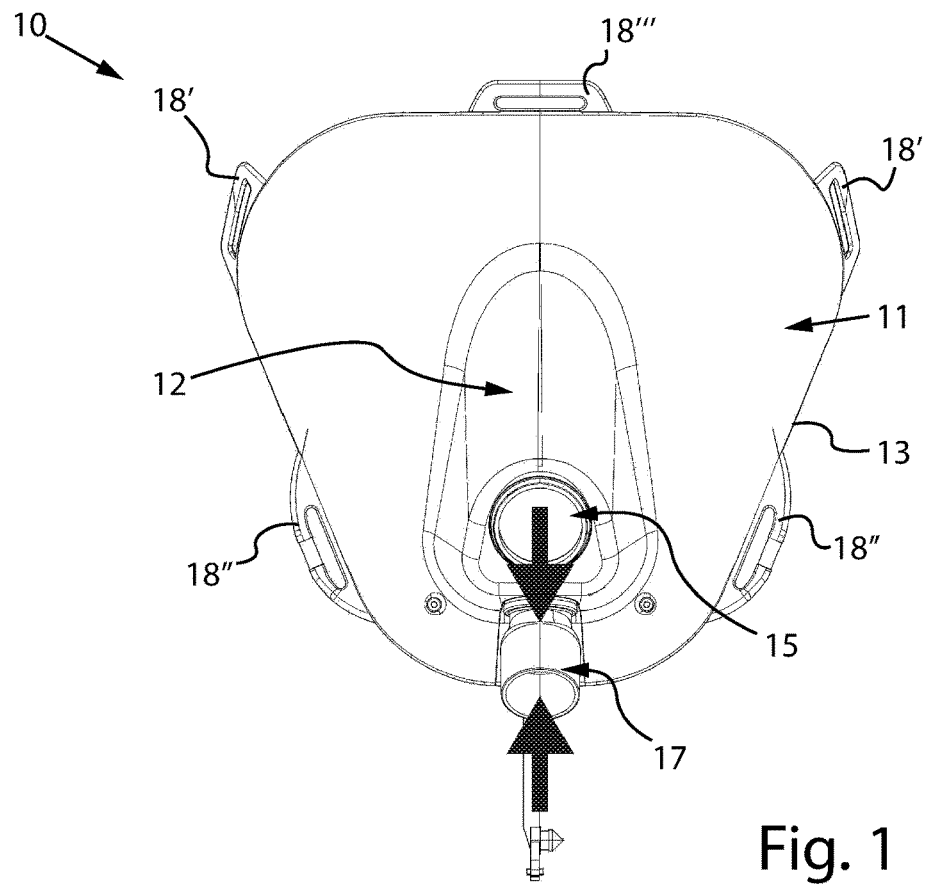
FIG. 1 shows a front view of a face mask according to the present invention.
Figure 2:
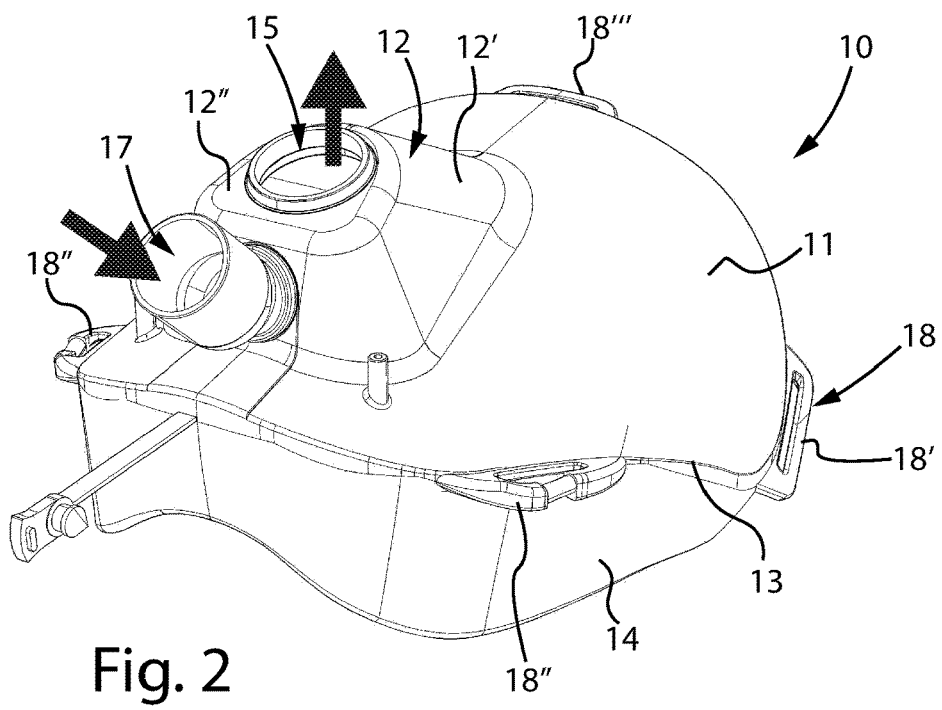
FIG. 2 shows a perspective view of the face mask according to the present invention.

With reference to the figures, a face mask for non-invasive respiratory therapy is shown, indicated as a whole by the reference numeral 10 and comprising a shaped shell 11 covering at least the mouth, nose and eyes of a patient once worn.

The shaped shell 11 is provided along a perimeter 13 with a sealing gasket 14 adapted to be placed in contact with the patient's face when the mask is worn.

The mask 10 according to the invention therefore preferably comprises the rigid shaped shell 11 made of transparent polycarbonate (PC) or copolyester (PETG), and the gasket 14, preferably overmoulded, made of thermoplastic elastomer (TPE).

Other materials according to the knowledge of the person skilled in the art can also be used alternatively or in conjunction with those just mentioned by way of example.

The shaped shell 11 is also advantageously provided with at least an inlet fitting 17 for the mixture of air and oxygen coming from a ventilation apparatus, not shown, through a pipe, and an outlet fitting 15 for the outlet of the air, rich in carbon dioxide, exhaled by the patient.

The outlet fitting 15 will preferably be of the so-called "non-vented" type, i.e. not provided with a hole for the escape of the carbon dioxide exhaled by the patient, which will instead be evacuated from the mask through said outlet fitting 15.

According to a preferred embodiment of the present invention, the shaped shell 11 comprises a shaped portion 12 projecting from the front surface of said shell 11 towards the outside, approximately centrally, configured so as to be substantially at the nose and mouth of the patient when the mask 10 is worn.

Preferably, said shaped portion 12 comprises a conical section 12' terminating with an outer front surface 12".

According to the preferred embodiment of the face mask 10 according to the present invention illustrated herein by way of example in the accompanying figures, said outlet fitting 15 is formed on said front surface 12" of said shaped portion 12, and said inlet fitting 17 is formed on said conical section 12' of said shaped portion 12.

More in particular, said inlet fitting 17 for the air is obtained on said conical section 12' of said shaped portion 12 on the lower part with respect to said outlet fitting 15.

The mask 10 according to the invention also preferably comprises a neckband, not shown in the figures, provided with a plurality of prongs.

In order to allow the attachment, in a fixed or removable manner, of this neckband to the mask, the mask 10 according to the present invention will comprise on said perimeter 13 of said shell 11 a plurality of attachment points 18.

The neckband preferably consists of a belt system configured to wrap the patient's nape when the mask is worn. Through the neckband, the mask 10 is firmly fixed on the patient's face to obtain the pneumatic seal of the gasket 14 on the face.

According to a preferred embodiment of the present invention, the shaped shell 11 comprises five attachment points 18 for the neckband, in which two upper attachment points 18' are placed in an upper portion of said shell 11 so that, when the mask is worn, they are at the level of the patient's eyes, symmetrically arranged with respect to a sagittal plane; two lower attachment points 18" are placed laterally in the lower portion of the shell 11 so that, when the mask is worn, they are at the level of the patient's chin, symmetrically arranged relative to a sagittal plane; and a fifth attachment point 18''' is placed centrally along the upper portion of the perimeter 13 of the mask 10, placed in the sagittal plane, so as to be at the patient's forehead when the mask is worn.

According to a further aspect of the present invention, the face mask 10 for the non-invasive respiratory therapy according to the present invention comprises a dedicated access, not shown, for a nasogastric tube obtained directly on the shaped shell 11.

Said dedicated access may preferably consist of a hole to which an elastic membrane is stably applied, such membrane being provided in turn with an expandable hole and with a closure cap for said hole.

The elastic membrane may preferably be made in one piece with the shaped shell 11 by overmoulding a thermoplastic elastomer (TPE), so that the elastic membrane is an integral and indissoluble part of the shaped shell 11 of the mask itself and does not risk being separated therefrom due to the positive pressure inside the mask.

In a bench test, a total face mask of the full face type known from the prior art, and the new face mask 10 according to the present invention, were then applied to a dummy connected to a breathing simulator (IngMar Medical ASL 5000).

A known stream of CO2 was fed to the dummy's trachea.

Figure 3:
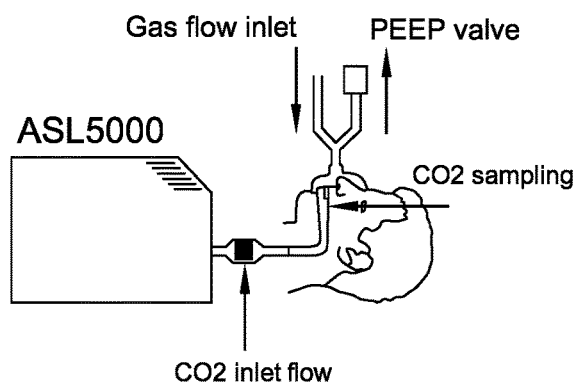
FIG. 3 shows a diagram of the test modes with which the mask according to the present invention and a mask of the known type have been tested.
Figure 3:
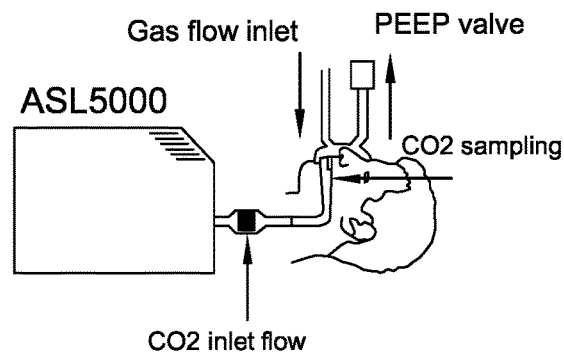
Figure 3:
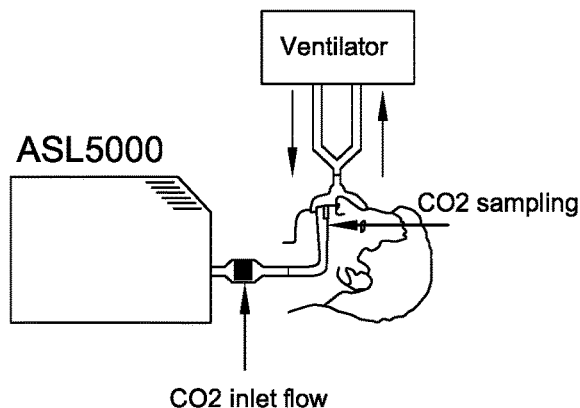
Figure 3:
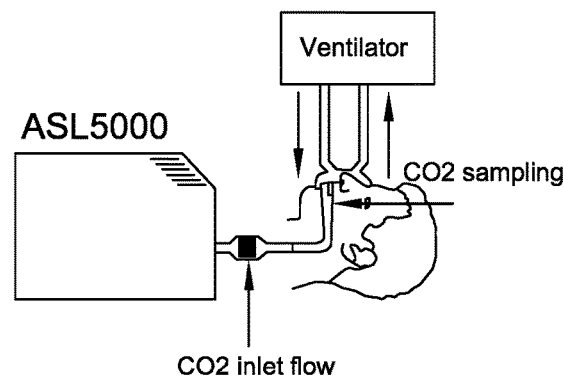

Several combinations of the ventilation parameters were tested, as shown in the diagram in FIG. 3: CPAP with continuous flow from 60 to 90 l/min and PEEP mechanical valve (the PEEP valve is a device for maintaining the positive expiratory end pressure) at 8 cmH2O, pressure support PSV of 6 and 11 cmH2O (Medtronic Puritan Bennett 840) with zero and 15 l/min Flow-By), respiratory rate of 15 and 30 bpm and CO2 flow rates of 200 and 300 ml/min, Current Volume or Tidal Volume set to 500 ml.

Airway pressure, airflow and $CO_2$ concentration (and CO2 flow as a product of the two) were recorded.

Figure 4:
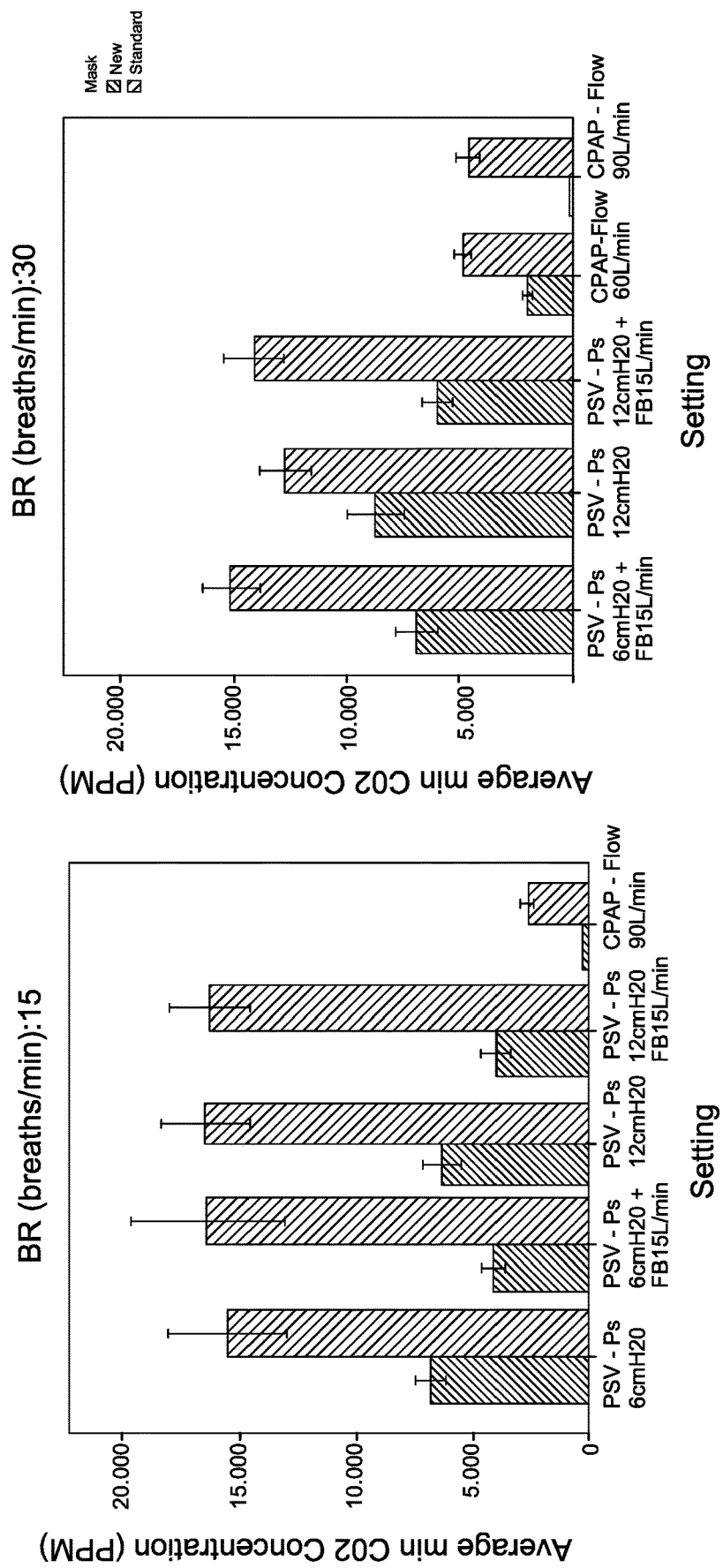
FIGS. 4 and 5 show the results of the ventilation tests conducted by the Applicant, in particular the performances of a traditional single-fitting full face mask and of the new face mask according to the present invention are presented.
Figure 5:
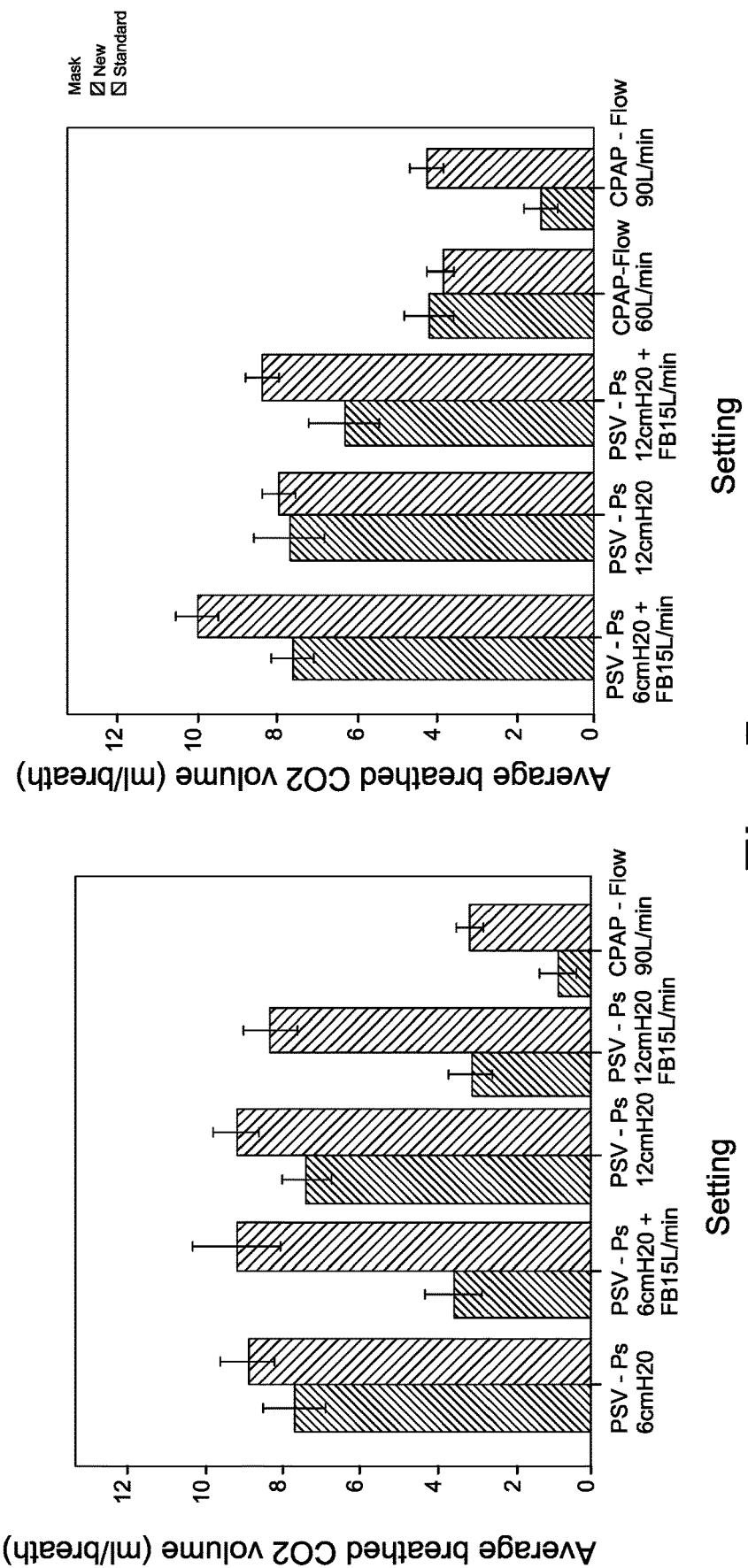

As shown in the graphs in FIGS. 4 and 5, in which the results of the ventilation tests conducted by the Applicant are presented, the average volume of $CO_2$ re-breathed (rebreathing) by the patient and the minimum concentration of inspiration of $CO_2$ are significantly lower with the new mask compared to the traditional mask, in all the conditions examined, with the exception of two conditions, currently subjected to verification to confirm the validity of the data and determination of the causes.

The bias flow of 15 l/min significantly reduced the rebreathing of $CO_2$ with the new mask, while it had no effect with the traditional mask.

The features of the face mask for non-invasive respiratory therapy with low value of $CO_2$ rebreathing object of the present invention, as well as the relative advantages are clear from the description given herein.

By way of example, among the main advantages of the mask according to the invention, it can be noted that the presence of the two inlet and outlet fittings 17, allows different configurations of the mask, not possible with known masks having only one fitting.

For example:

in the configuration with a double-pipe ventilator, the two ventilator pipes will be connected to each fitting 15, 17;

in the configuration for CPAP with single-pipe ventilator or CPAP generator it is possible to connect to the inlet fitting 17 the ventilator pipe and a PEEP valve to the outlet fitting 15;

in the configuration for CPAP with Venturi generator it is possible to connect the venturi to the inlet fitting 17 and a PEEP valve to the outlet fitting 15.

Moreover, it is clear that the face mask according to the present invention thus conceived is susceptible to numerous modifications and variations, all falling within the invention; moreover, all details can be replaced with technically equivalent elements.

In particular, the materials described as well as the sizes, can be whatever, according to the technical requirements.

The invention claimed is:

1. A face mask for non-invasive respiratory therapy of the full face type, comprising:
    a shaped shell configured so as to cover at least the mouth, the nose and the eyes of a patient when the mask is worn, said shaped shell having a perimeter provided with a sealing gasket,
    wherein said shaped shell comprises at least one inlet fitting for the connection to a pipe through which a ventilation apparatus supplies the mask with a mixture of air and oxygen, and at least one outlet fitting, separate from said inlet fitting, for the discharge of air exhaled by the patient,
    wherein said shaped shell comprises, approximately centrally, a shaped portion projecting from the front surface of said shell towards the outside, configured so as to be substantially at the nose and mouth of the patient when the mask is worn,
    wherein said shaped portion comprises a conical section and an outer front planar surface at an end of the conical section,
    wherein said outlet fitting for exhaled air extends from a first opening in said outer front planar surface of said shaped portion, and
    wherein said inlet fitting for the air coming from said ventilation apparatus extends from a second opening in a wall of said conical section of said shaped portion, the second opening being positioned lower on the shaped shell with respect to the outer front planar surface.

2. The face mask according to claim 1, further comprising on said perimeter of said shell a plurality of attachment points for the attachment of a neckband.

3. The face mask according to claim 2, wherein the plurality of attachment points includes five attachment points.

4. The face mask according to claim 3, wherein one of the attachment points is an attachment point centrally placed along the upper section of the perimeter of the mask, in the sagittal plane, such as to be in a substantially centered position on the forehead of the patient when the mask is worn.

5. The face mask according to claim 1, further comprising, on said shaped shell, a dedicated access for a nasogastric tube.

6. The face mask according to claim 5, wherein said dedicated access for a nasogastric tube consists of a hole to which an elastic membrane is stably applied, such membrane being provided in turn with an expandable hole and with a closure cap for said hole.

7. The face mask according to claim 1, wherein the first opening of the outlet fitting is positioned entirely above the second opening of the inlet fitting on said shaped portion.

8. The face mask according to claim 1, wherein the outlet fitting and the inlet fitting are positioned on said shaped portion such that the air exhaled does not pass through the second opening of the inlet fitting.

* * * * *